US005645547A

United States Patent [19]
Coleman

[11] Patent Number: 5,645,547
[45] Date of Patent: Jul. 8, 1997

[54] REVISABLE INTERFERENCE SCREW

[75] Inventor: R. Glen Coleman, Clearwater, Fla.

[73] Assignee: Linvatec Corporation, Largo, Fla.

[21] Appl. No.: 230,561

[22] Filed: Apr. 20, 1994

Related U.S. Application Data

[62] Division of Ser. No. 987,477, Dec. 7, 1992, Pat. No. 5,354,299.

[51] Int. Cl.⁶ .................................................. A61B 17/86
[52] U.S. Cl. ........................... 606/73; 606/86; 606/104
[58] Field of Search ............................. 606/73, 72, 60, 606/65, 66, 98, 99, 104; 411/388, 389, 395, 405, 407, 408, 410, 424, 425; 81/439, 459, 436

[56] References Cited

U.S. PATENT DOCUMENTS

| | | |
|---|---|---|
| 2,242,003 | 5/1941 | Lorenzo . |
| 2,267,925 | 12/1941 | Johnston . |
| 2,570,465 | 10/1951 | Lundholm . |
| 3,892,232 | 7/1975 | Neufeld . |
| 4,349,929 | 9/1982 | Dewey .......................... 81/439 X |
| 4,463,753 | 8/1984 | Gustilo . |
| 4,537,185 | 8/1985 | Stednitz . |
| 4,754,749 | 7/1988 | Tsou . |
| 4,790,850 | 12/1988 | Dunn et al. . |
| 4,858,601 | 8/1989 | Glisson . |
| 4,870,957 | 10/1989 | Goble et al. . |
| 4,927,421 | 5/1990 | Goble et al. . |
| 4,950,270 | 8/1990 | Bowman et al. . |
| 5,102,276 | 4/1992 | Gourd ........................... 411/395 X |
| 5,116,337 | 5/1992 | Johnson . |
| 5,139,499 | 8/1992 | Small et al. . |
| 5,139,520 | 8/1992 | Rosenberg . |
| 5,151,104 | 9/1992 | Kenna . |
| 5,152,764 | 10/1992 | Goble . |
| 5,152,790 | 10/1992 | Rosenberg et al. . |
| 5,156,616 | 10/1992 | Meadows et al. ............ 606/232 |
| 5,169,400 | 12/1992 | Muhling et al. . |
| 5,203,784 | 4/1993 | Ross et al. . |
| 5,209,753 | 5/1993 | Biederman et al. . |
| 5,211,647 | 5/1993 | Schmieding . |
| 5,364,400 | 11/1994 | Rego, Jr. et al. ............... 606/72 |

FOREIGN PATENT DOCUMENTS 8909030 10/1989 WIPO .
9008510 8/1990 WIPO .

*Primary Examiner*—Guy V. Tucker
*Attorney, Agent, or Firm*—Michael de Angeli

[57] ABSTRACT

A surgical interference screw includes an axial bore extending entirely through the screw and hexagonally or otherwise configured at least at its ends to be drivable from either end. A driver includes a shaft with a forward bone penetrating tip. The screw is slid onto the shaft to expose the tip forwardly of the screw prior to inserting the screw into bone tissue. The forward portion of the shaft has a hexagonal or other periphery to engage the bore and turn the screw. The top of the shaft protruding from the end of the screw may be variously shaped as a trocar, pick, twist-drill bit, or gimlet thread. Plural drivers may be provided with different tips for various tasks. The relatively thick shaft and long engagement area between the screw and driver prevent screw mis-alignment and loss. The hexagonal or similar socket at least at both ends of the screw permits engagement by the driver and revision from either end. Irrespective of which end is driven, the screw can be revised in either direction.

33 Claims, 2 Drawing Sheets

REVISABLE INTERFERENCE SCREW

This application is a divisional application of U.S. patent application Ser. No. 07/987,477, filed Dec. 7, 1992, now U.S. Pat. No. 5,354,299.

BACKGROUND OF THE INVENTION

1. Technical Field

The present invention relates to surgical interference screws, especially those used in ligament reconstruction.

2. Discussion of the Prior Art

Interference screws are surgical screws that interfere or wedge between bones or other firm tissue. A typical use is in reconstructing the anterior cruciate ligament of the knee whereby a tunnel is drilled into the femur, and the ligament is inserted and secured inside the tunnel. The other end of the ligament is inserted similarly into the tibia. Procedures for reconstructing this ligament are described in U.S. Pat. No. 5,139,520, issued to Rosenberg on Aug. 18, 1992, and in U.S. Pat. No. 4,927,421, issued to Goble et al, on May 22, 1990. The disclosures from both of these patents are incorporated herein by reference.

The ligament (either graft or prosthetic ligaments can be used) may, for example, terminate in a bone block or bone plug fixed inside the tunnel by the interference screw. Alternatively, the ligament may terminate An a suitable polymer (or other firm material) block or plug serving as an attachment point for the ligament. The screw is driven into the gap between the tunnel wall and the bone plug to wedge the bone plug in place.

Interference screws often become skewed (i.e., turn aside from their intended direction) if they are started at the wrong angle or meet an obstacle. Also, the interference screw may disengage from its driver and become lost in the patient's body. When the screws are used in endoscopic operations, as is typical, these difficulties are multiplied, and the proper starting position may be difficult to locate as well.

Guide wires are often employed to prevent interference screws from being lost or mis-aligned. The wire is fed into the bone tunnel between the tunnel wall and bone plug. By means of an axial cannula extending the length of the interference screw, the screw is slid over the emplaced wire to bring the screw to the proper bone entry point and help keep the screw aligned with the intended path.

Interference screws usually form their own threads in the engaged bone tissue by cutting and removing material. To rotate the interference screw and force the threads into the bone, a special driver is used and includes a cannula with a transverse cross-section identical to that of the interference screw. The guide wire passes through both the screw and driver and allows the driver to engage the socket with the guide wire in place.

An interference screw usually has no screw head extending transversely beyond the shank radius in order to permit the entire screw to be driven into the bone tissue. Accordingly, the threads generally, but not necessarily, run all the way from the distal point to the rear of the screw, and no structure extends laterally beyond the minor screw thread diameter. Instead of a slot, cross, or Phillips head, a female drive socket, usually hexagonal, is provided at the rear end of the interference screw.

The diameter and strength of the guide wire are limited by the use of a female socket and a male driver which must contain the guide wire within. Given that the screw has a certain diameter and a certain thread height, the shank diameter (i.e., the minor thread diameter) is thereby fixed. Around the rear socket, a minimum wall thickness is needed for mechanical strength, so the outermost points of the socket define a first circle having a diameter equal to the shank diameter minus the wall thickness. The socket must be contoured to engage the driver; for example, it might be starred, lobed, squared, hexagonal, etc. The innermost points of the socket (i.e., those socket points of least radius) define a second circle of smaller diameter. The driver must be slightly smaller than the engaged socket, so the innermost points of the driver lie on a third circle of diameter smaller than that of the innermost points of the socket. The wall of the driver shaft, between the innermost driver points and the driver cannula, must be of substantial thickness if the driver is not to bend or buckle in use, so the cannula defines a fourth circle of diameter smaller still. The guide wire itself is smaller than the cannula of the driver for clearance. All these reductions mean that the guide wire diameter is severely limited in relation to the screw diameter which itself is generally only a few millimeters. The severely limited guide wire diameter lowers its stiffness and resistance to kinking. Specifically, wire strength varies with the square of its diameter, so that if the diameter is halved, the strength is quartered. Accordingly, the small diameter of interference screws places strict limits on guide wire strength.

Screws often skew when started and burrow into the bone in the wrong direction unless they are held in alignment while being driven. The guide wire is too weak to hold the interference screw properly; that is, the wire can bend or kink permanently under the strong lateral forces sometimes exerted during screw advancement. The guide wire can also kink when being fed into the bone tunnel. Engagement of the driver tip with the socket helps to align the screw, but the engagement length is typically so short that the driver tip cannot secure the interference screw alignment.

In addition to the risk of the screw turning from its path, guide wires have the additional problem of being hard to emplace. In view of the fact that the wires are flexible and can whip about, the surgeon cannot easily discern, from the orientation of the observed portion, the direction in which the wire tip is pointing.

A refinement of the guide wire method for keeping an interference screw aligned is described in the '421 Goble et al. patent, mentioned above. Goble et al discloses an interference screw having an integral drill bit at the forward end and a helical thread wound about only the rear portion of the screw. The bit has a diameter equal to the minor diameter of the thread. The guide wire, cannula, hexagonal socket, and driver are conventional. The Goble et al interference screw is held in alignment only by the bit in its bored hole, the guide wire, and the driver inserted in the screw socket. However, the engaged driver bit is short and can cut sideways as well as forwardly. Further, the Goble et al bit has tapered flutes for rearwardly directing cut bone chips between the threads in the region where the threads are exerting great force against the bone. If the interference screw is to penetrate far into bone, the cutting action may be decreased when the chips fill the flutes and jam under the cutting edge. The sharp cutting edge of the Goble et al bit can also irritate or tear soft tissues, such as ligaments and muscles, if the interference screw should migrate out of the bone or be emplaced wrongly.

A further refinement is marketed by Acumed, Inc. as the Oregon Fixation System. This system employs a fixation screw having an integral elongated guide member projecting forwardly from its distal end with a transverse dimension significantly smaller than the root diameter of the screw. The guide member is described in promotional literature as "assuring ease of use and accurate placement eliminating the need for guide pins". The proximal end of the screw is provided with a hexagonal socket for receiving a hexagonal driver. This system is an improvement over systems using guide wires but still does not have the inherent stability during insertion, nor the flexibility for screw revision, of the present invention as described hereinbelow.

Another drawback to conventional interference screws is that they cannot be revised easily. The screw may need to be revised if the ligament graft fails, the screw migrates, or some other problem develops after the surgery. A cannulated interference screw, if successfully emplaced by the use of a guide wire, is left in place after the wire is withdrawn. With the wire withdrawn, there is nothing to guide the driver back to the screw socket in order to turn the screw back out. Unguided location of the socket is difficult because the socket is a small target, the screw is surrounded by hard bone which feels like the screw when probing, and the blunt-tipped hexagonal driver must be used to probe instead of a pointed instrument that could more easily find the socket. Moreover, the bone tunnel begins to fill with new tissue, thereby imprisoning the screw, as time elapses after the original surgery. All of this makes revision difficult. The previously withdrawn guide wire that was used to guide the interference screw into the gap is useless during revision, since it is even more difficult to thread the guide wire into the screw cannula than to put the driver into the emplaced socket.

In reconstructing the anterior cruciate ligament of the knee, it may be impractical for the driver to approach the screw for revision from the originally driven end, depending upon the original screw placement and how much tissue growth has occurred in the tunnel since completion of the operation. It is desirable, therefore, for a surgeon to be able to approach the interference screw from either end in order to remove it. However, no prior art interference screw can accept a driver at the forward tip.

In sum, the guide wires and prior art interference screws do not present a satisfactory answer to the problem of interference screw angular stability when driving or to the problem of revising interference screws after emplacement.

OBJECTS AND SUMMARY OF THE INVENTION

It is therefore a primary object of the present invention to provide an easily revisable interference screw.

It is another object of the invention to provide an interference screw that can be driven straight and will not skew off course.

It is a further object of the invention to provide an interference screw requiring no guide wire.

Still another object of the present invention is to provide an interference screw capable of being driven from either end.

It is also an object of the present invention to provide an interference screw and driver combination having interchangeable utility in various tissues or operations.

In accordance with the present invention, an interference screw includes an axially centered bore having at least a portion of its length prismatically configured, the bore extending longitudinally through the entire screw. The prismatic configuration can be hexagonal, star-shaped, lobed, etc., and is configured to be driven by a driver having a forward portion with an elongated correspondingly prismatic configuration. The forward shaft portion slides into and mates with the prismatic section of the interference screw bore for torque transmission when a surgeon grasps the driver handle and rotates the shaft to drive the interference screw into bone tissue. No guide wire is used.

The driver may include a stop or seat against which the interference screw comes to rest when it is slid onto the driver forward portion. When the interference screw is thusly seated, the distal end or tip of the driver forward shaft portion protrudes from the distal end of the screw. This protruding tip may have various configurations for different applications, namely: twist-drill, thread-tapping trocar, gimlet (spiral thread), pick, and so on. The interference screw can engage any one of a set of drivers, each having a tip adapted to the specific application, procedure, or tissue.

The pick-ended driver has particular utilization during revision of an interference screw. Specifically, the projecting sharp point makes it easy to locate the screw bore by probing in the bone tunnel, after which the prismatic drive section of the shaft is slidably engaged with the screw bore by pushing the driver forward.

In one embodiment of the invention, the interference screw is prismatic at its front and rear ends. In another embodiment the bore is prismatic throughout its entire length. In either case, during revision, the screw can be probed and driven from either end. If approached from its leading end, revision can be effected either by: backing the screw out of the bone tunnel, back end first, from the leading end of the screw; or drawing the screw out of the tunnel, leading end first, also from the leading end of the screw.

The length of the driver between the seat and the protruding tip can be wholly prismatic. It can also include a prismatic section adjacent the seat followed by a cylindrical section toward the tip. Such a two-section driver can be advantageously used with the corresponding interference screw embodiment having a central cylindrical section and prismatic female drive sockets located at one or both screw ends and configured to accept the similarly-shaped male prismatic section of the driver.

The above and still further objects, features and advantages of the present invention will become apparent upon consideration of the following detailed description of specific embodiments thereof, particularly when considered in conjunction with the accompanying drawings wherein like reference numerals in the various figures are utilized to designate like components.

DESCRIPTION OF THE PREFERRED EMBODIMENTS

Figure 1:
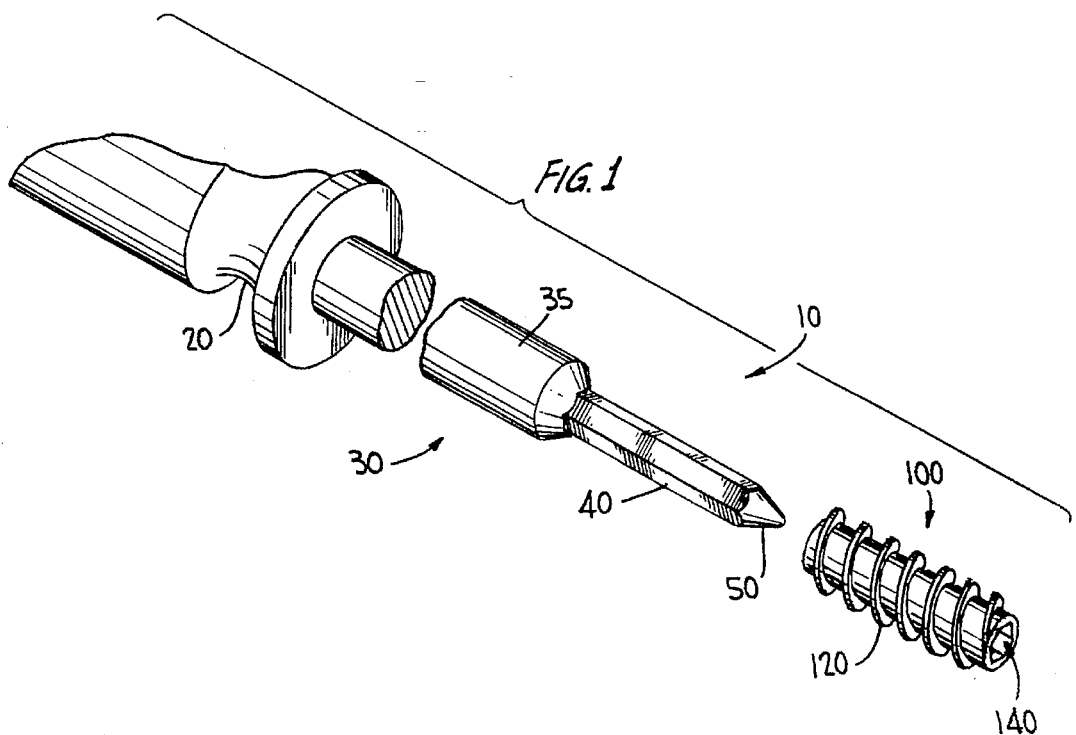
FIG. 1 is an exploded view in perspective of a driver with a blunt tapered point and an interference screw according to the present invention.

An interference screw 100 according to the invention is shown in FIG. 1 exploded axially from a forward portion 40 of a shaft 30 of a driver 10. Shaft 30 extends from a handle 20 to a point 50, and includes forward portion 40. Screw 100 has an external helical thread 120 and an internal axial bore 140 into which forward shaft portion 40 may be inserted to drive the screw. Bore 140 and forward portion 40 are both hexagonal in the illustrated embodiment, but they may have any shape suitable for transmitting torque from driver 10 to screw 100. In this regard, the shapes of both bore 140 and forward portion 40 are described herein as "prismatic". It is to be understood that this term, for purposes of this disclosure and the attached claims, is not limited to shapes with regular polygonal transverse cross-sections; rather, any configuration precluding relative rotation between the screw and the inserted driver is intended to be covered by "prismatic".

Shaft 30 has an increased diameter at a shoulder or stop member 34 between the main portion of shaft 30 and forward portion 40. Shoulder 34 acts as a seat for the proximal end of screw 100 when the screw slides onto forward portion 40, thereby preventing the screw from moving further toward handle 20.

Figure 9:
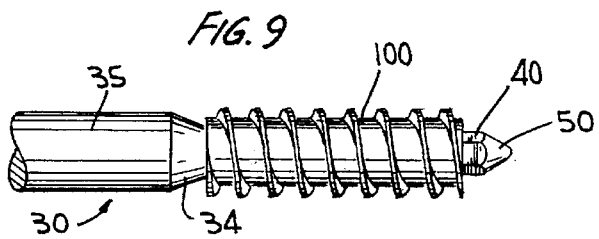
FIG. 9 is a side view in elevation of the interference screw of the present invention engaged by a driver of the present invention.

As illustrated in FIG. 9, the respective lengths of the interference screw 100 and the forward portion 40 are such that, when screw 100 rests against shoulder 34, the distal end of portion 40 protrudes from screw bore 140. This protruding distal end part is denominated herein as tip 50 of the driver 10.

Forward portion 40 and tip 50 may take a variety of configurations, as seen in FIGS. 1 through 6, respectively depicting a relatively blunt point 50 a fluted cutting point 50a and forward portion, a gimlet or spiral point 50b, a trocar point driver 50c, a forward portion resembling a twist drill bit 50d, and a sharp point 50e for probing. Each of these configurations of forward portions 40 and tips 50 may be used to achieve their indicated functions with the screw 100.

Figure 3:
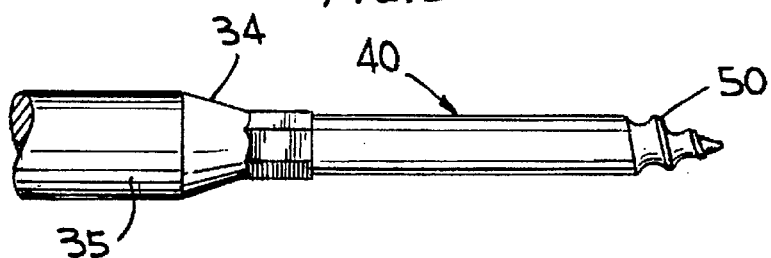
FIG. 3 is a side view of the forward end of a gimlet or spiral-point driver useful with the screw of FIG. 1.
Figure 4:
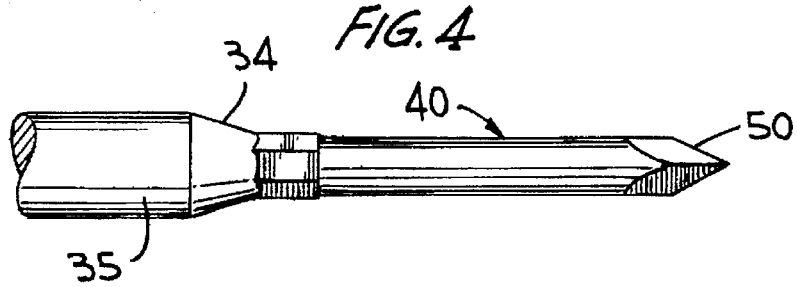
FIG. 4 is a side view of the forward end of a trocar-point driver useful with the screw of FIG. 1.
Figure 5:
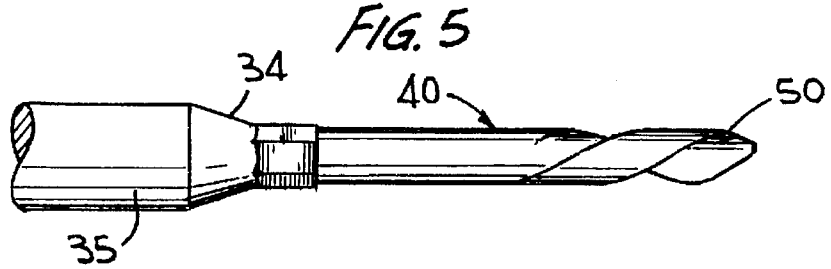
FIG. 5 is a side view of the forward end of a drill bit-point driver useful with the screw of FIG. 1.

It will be noted that each of the forward portions 40 shown in FIGS. 3, 4 and 5 includes a hexagonal cross section extending only partially along forward shaft portion 40. This embodiment may be employed to particular advantage with the twist-drill pointed embodiment of driver 10 shown in FIG. 5, since the spiral flutes of such a shaft are more easily formed into a cylindrical shape than into a prismatic shape.

Figure 7:
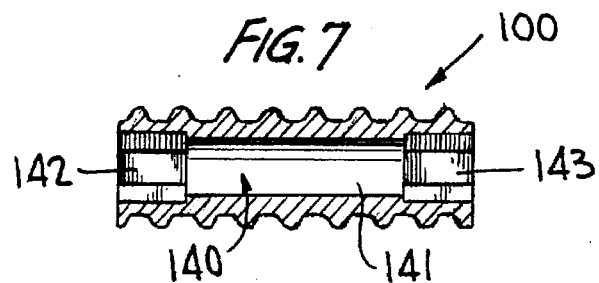
FIG. 7 is a side view in longitudinal section of one embodiment of the interference screw of the present invention.

Referring to FIG. 7, an interference screw 100 of the present invention includes a bore 140 disposed concentrically about the longitudinal axis of the screw and having a central cylindrical intermediate section 141 and hexagonal end sections 142, 143. This embodiment may be employed with the partially-prismatic forward shaft portions 40 of the drivers shown in FIGS. 3, 4 and 5. Such forward portions are not restricted to use with this embodiment, however, nor conversely is the embodiment with intermediate cylindrical section 141 restricted to use with these forward shaft portions.

Figure 8:
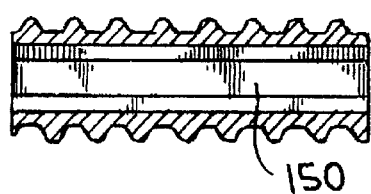
FIG. 8 is a side view in longitudinal section of another interference screw embodiment of the present invention.

Another embodiment of the interference screw of the present invention is illustrated in FIG. 8. Screw 110 differs from screw 100 only in that the entirety of its longitudinal bore 150 is prismatic (e.g., hexagonal in transverse cross-section) so as to engage the correspondingly contoured forward portion of the driver.

One important advantage of the present invention is that alignment of the interference screw is assured during insertion. The screw cannot mis-align without bending the driver shaft; that shaft, in turn, is much stronger than a guide wire and can easily withstand the forces applied by a surgeon. Specifically, driver shaft forward portion 40 has a diameter at least twice that of a typical guide wire, thereby at least quadrupling its strength.

The wider part 35 of shaft 30 intermediate handle 20 and forward portion 40 can be greater in diameter and stronger than forward portion 40. The diameter of part 35 can increase to at least the interference screw shank diameter without increasing the driving resistance of interference screw 100, 110. The resulting increase in strength over a guide wire is at least ten times, and may be as much as fifty times.

It is clear that a shaft that is stiffer by at least a factor of ten than the wire, and tipped with a very short section having at least double the stiffness, will allow interference screw 100 to be at all times aligned with driver 10. Unlike a guide wire that can bend, driver 10 will never have its tip 50 oriented at an angle different from that of handle 20. The slight clearance between forward portion 40 and bore 140 allows, over the entire length of screw 100, 110, only minimal angular wobbling. Unlike prior-art interference screws having short sockets, screw 100, 110 will never be substantially misaligned with the driver. The common trouble of interference screws skewing when being driven is avoided by the present invention, which holds the screw at the angle of the shaft as precisely as possible by employing the greatest possible engagement length.

A related prior art problem is that the screw may inadvertently fall off the driver and be lost in the patient's body. The present invention, with its elongated engagement between surfaces of the screw and driver shaft, lessens the chance of this occurring.

Another and distinct advantage of the present invention is that a variety of configurations of tip 50 is readily provided for different procedures and materials, or where the interference screw is required to sequentially traverse different tissues of varying hardness. Piercing, drilling, or probing can all be interchangeably accomplished simply by removing one driver and replacing it with another. On the other hand, only one type of interference screw needs to be stocked and used; the variation in tips, which in the prior art was embodied in various screw types, is in the present invention embodied in the reusable drivers. This is a distinct advantage because the drivers are much larger than the screws, making them easier to select and manipulate. For this purpose the drivers may be clearly labeled or color-coded. With prior-art interference screws, a selection of interference screws would have to be stocked in the operating room if screws with various points were needed; the difficulties of color-coding or labeling small surgical screws are evident. The trouble of manipulating such screws, and the danger of mix-ups, is also clear.

A third major advantage resides in the driver being readily inserted into the interference screw from either end for revision. This feature is particularly useful, as discussed above, in anterior cruciate ligament reconstruction of the knee, where the inserted screw cannot be approached from the same direction as in the original operation (i.e., from the intercondylar notch of the knee joint). The socket at the lead end of the screw allows it to be approached from the lateral side of the femur with the "pick" or guide point, shown in FIG. 6, thereby facilitating location of the bore of the screw for engagement with the driver to effect revision. Once the screw is engaged it can be backed out through opening in the bone tunnel at the intercondylar notch by driving the screw from the tunnel opening at the lateral side of the femur. Alternatively, the screw can be drawn through the opening at the femur by driving the screw from that opening. Of course, if the trailing end of the screw is accessible, revision may be effected by driving the screw from that end in a conventional manner.

Figure 2:
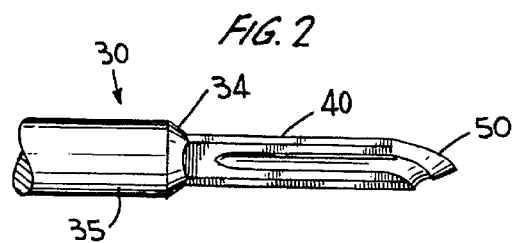
FIG. 2 is a side view of the forward end of an alternative driver with a fluted tip and forward portion useful with the screw in FIG. 1.
Figure 6:
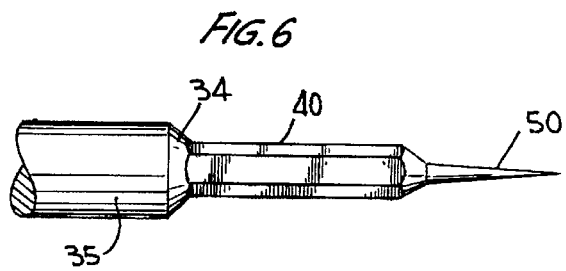
FIG. 6 is a side view of the forward end of a pick-point driver useful with the screw of FIG. 1.

A further advantage of the present invention is seen in the long chip flutes in the driver tip 50a and 50d and forward shaft portion 40 shown in FIGS. 2 and 5, respectively. The flutes may be extended as far back as necessary to accommodate the removed bone chips, thusly preventing jamming of the driver shaft in the screw by chip build-up. If desired, the diameter of the shaft may also be reduced to less than the minor diameter of the interference screw threads to create space between the interference screw and shaft for collecting the bone chips.

The interference screw 100, 110 of the present invention, unlike prior-art interference screws, can be fabricated by cutting a continuous length of threaded, bored tubing. A sharp cutting edge is formed by such a cut. The screw, with its hexagonal or otherwise prismatic bore configuration at both ends, is substantially symmetrical about a plane perpendicularly bisecting its longitudinal axis. Accordingly, both ends of the screw can be the leading or trailing edge.

Shaft 30 ordinarily will be fairly long for angular control, but may be very short for special applications, such as where the screw insertion depth is to be limited. In extreme cases, shaft 30 may consist entirely of forward portion 40 and tip 50.

Tip 50 can be of the same cross-section as forward portion 40, if desired.

Although the preferred embodiment has been described in terms of a screw having a single thread, two or more threads may be used, if desired.

Handle 20 may have any suitable shape, such as a T-handle or knob. Further, it may be replaced by a tool, such as a rachet, torque wrench, electric drill or driver, air-motor tool, etc. The term "torque tool" as used herein includes all sorts of handles for manipulation, as well as all power tools and drivers capable of exerting a torque. "Torque tool means" includes both torque tools and any structure for connection to a torque tool.

The present invention provides an interference screw that may be driven from either end, thereby providing the surgeon with the option of approaching the screw, for purposes of revision, in the more accessible direction. Moreover, the screw can be revised in either direction whether driven from its leading end or trailing end.

Having described preferred embodiments of a interference screw in accordance with the present invention, it is believed that other modifications, variations, and changes will be suggested to those skilled in the art in view of the teachings set forth herein. It is therefore to be understood that all such variations, modifications, and changes are believed to fall within the scope of the present invention as defined by the appended claims.

What is claimed is:

1. In combination:
   a surgical self-tapping interference screw having a shank with a central longitudinal screw axis and first and second ends, at least one exterior helical thread extending substantially the entire length between said first and second ends, and a bore defined longitudinally and coaxially throughout the entire length of said shank between said first and second ends, said bore having a cross-sectional shape at least at both ends thereof to receive a driver for transmission of torque, said screw being substantially symmetrical; and
   a driver for rotating and axially advancing said interference screw, said driver comprising a handle responsive to applied torque for rotating said driver about a longitudinal driver axis, a shaft rigidly extending forwardly from said handle and sized to fit in said bore, and an integral tip of reduced cross-sectional area disposed at the distal end of said shaft, and terminating at a forward point;
   wherein said shaft is peripherally configured to engage at least part of said bore to preclude rotation of said shaft relative to said interference screw when said shaft is disposed in said bore;
   wherein said shaft includes a stop member spaced from said handle and defining an axial insertion limit position of said shaft through said bore, said stop member being situated proximally from said tip by a distance equal to or greater than the length of said interference screw; and
   wherein said distal tip, with said screw at said insertion limit position of said shaft, extends axially beyond said bore to be exposed distally of said interference screw.

2. The combination according to claim 1 wherein said shaft has a prismatic peripheral configuration, and wherein said bore has a correspondingly prismatic configuration along at least part of the length of said bore.

3. The combination according to claim 2 wherein said prismatic configuration and correspondingly prismatic configuration have hexagonal transverse cross-sections.

4. The combination according to claim 2 wherein said bore has said correspondingly prismatic configuration throughout the entire length of the bore.

5. The combination according to claim 2 wherein said shaft has said prismatic peripheral configuration only along a short portion of said shaft adjacent said stop member.

6. The combination according to claim 2 wherein said screw is substantially symmetrical about a plane radially bisecting said longitudinal screw axis.

7. The combination according to claim 6 wherein said tip is a sharpened cutting member for cutting bone tissue in contact therewith in response to rotation of said handle.

8. The combination according to claim 6 wherein said tip is a sharp pointed guide and pick member.

9. The combination according to claim 1 wherein when said screw shaft is at said insertion limit position, said bore is configured to be engaged by the periphery of said shaft at said first and second ends of said screw but not intermediate said first and second ends.

10. The combination according to claim 1 wherein said bore is configured to be engaged by the periphery of said shaft along the entire length of said screw.

11. The combination according to claim 1 wherein said screw is substantially symmetrical about a plane radially bisecting said longitudinal screw axis.

12. The combination according to claim 1 wherein said tip is a sharpened cutting member for cutting bone tissue in contact therewith in response to rotation of said handle.

13. The combination according to claim 1 wherein said tip is a sharp pointed guide and pick member.

14. The combination according to claim 1 wherein, when said screw is at said insertion limit position, said tip of said shaft of said driver and the end of said screw nearest said tip of said shaft together form a smooth tapered transition simulating an integral elongated non-cannulated guide member projecting forwardly from the distal end of said screw.

15. The combination according to claim 1 wherein said distal end of said driver shaft has at least a partially prismatic axial section and said tip has a non-prismatic, tapered tip.

16. In combination:

a surgical screw having a shank with a central longitudinal screw axis and first and second ends, at least one exterior helical thread extending substantially the entire length between said first and second ends, and a bore defined longitudinally and coaxially throughout the entire length of said shank between said first and second ends; and a driver for rotating and axially advancing said screw, said driver comprising a handle responsive to applied torque for rotating said driver about a longitudinal driver axis, a shaft extending forwardly from said handle and sized to fit in said bore, and a tip disposed at the distal end of said shaft;

wherein said shaft has a prismatic peripheral configuration;

wherein said shaft includes a stop member defining an axial insertion limit position of said shaft through said bore;

wherein said stop member is spaced from said tip a distance corresponding to the axial length of said screw so that at said insertion limit position of said shaft, said tip extends beyond said bore to be exposed distally of said screw;

wherein said bore has a correspondingly prismatic configuration along said first and second short axial sections of the bore extending from said first and second ends, respectively; and wherein said bore includes a longer cylindrical intermediate axial section extending between said first and second short axial sections.

17. In combination:

a surgical screw having a shank with a central longitudinal screw axis and first and second ends, at least one exterior helical thread extending substantially the entire length between said first and second ends, and a bore defined longitudinally and coaxially throughout the entire length of said shank between said first and second ends; and a driver for rotating and axially advancing said screw, said driver comprising a handle responsive to applied torque for rotating said driver about a longitudinal driver axis, a shaft extending forwardly from said handle and sized to fit in said bore, and a tip disposed at the distal end of said shaft;

wherein said shaft has a prismatic peripheral configuration;

wherein said bore has a correspondingly prismatic configuration along at least part of the length of said bore;

wherein said shaft includes a stop member defining an axial insertion limit position of said shaft through said bore;

wherein said tip, at said insertion limit position of said shaft, extends beyond said bore to be exposed distally of said screw;

wherein said screw is substantially symmetrical about a plane perpendicularly bisecting said longitudinal screw axis; and wherein said tip and said shaft comprise a drill bit for drilling into bone tissue in contact therewith in response to rotation of said handle.

18. In combination:

a surgical screw having a shank with a central longitudinal screw axis and first and second ends, at least one exterior helical thread extending substantially the entire length between said first and second ends, and a bore defined longitudinally and coaxially throughout the entire length of said shank between said first and second ends; and a driver for rotating and axially advancing said screw, said driver comprising a handle responsive to applied torque for rotating said driver about a longitudinal driver axis, a shaft extending forwardly from said handle and sized to fit in said bore, and a tip disposed at the distal end of said shaft;

wherein said shaft is peripherally configured to engage at least part of said bore to preclude rotation of said shaft relative to said screw when said shaft is disposed in said bore;

wherein said shaft includes a stop member defining an axial insertion limit position of said shaft through said bore;

wherein said tip, at said insertion limit position of said shaft, extends beyond said bore to be exposed distally of said screw; and wherein said tip and said shaft comprise a drill bit for drilling into bone tissue in contact therewith in response to rotation of said handle.

19. A unitary surgical self-tapping interference screw, said screw being substantially symmetric about a plane bisecting a longitudinal axis thereof, and consisting of:

a rigid shank with a central longitudinal screw axis and first and second ends;

at least one exterior helical self-tapping thread formed integrally with said shank between said first and second ends;

a bore being formed in said shank, said bore extending longitudinally and coaxially throughout the entire length of said shank between said first and second ends and said bore having a uniform continuous transverse cross-section extending from one end of said shank through to the other end thereof, for torque-transmitting engagement with a correspondingly-shaped driver inserted into said bore from either of said first and second ends.

20. The surgical screw according to claim 19 wherein said bore in said screw has a uniform transverse cross-section throughout its entire length.

21. The surgical screw according to claim 20 wherein said uniform cross-section is hexagonal.

22. The surgical screw according to claim 19 wherein said bore has a first transverse cross-section adjacent each of said first and second ends, and a second transverse cross-section intermediate said first and second ends.

23. The surgical screw according to claim 22 wherein said first transverse cross-section is hexagonal and said second transverse cross-section is circular.

24. The surgical screw according to claim 19 wherein said bore has a first transverse cross-section adjacent said first end and a second transverse cross-section throughout most of its length.

25. The surgical screw according to claim 19 wherein said helical thread extends substantially the entire length of said shank.

26. A surgical interference screw consisting of:
a unitary rigid shank with a central longitudinal screw axis and first and second ends;
at least one exterior helical thread formed integrally with said shank and extending substantially continuously between said first end and said second end;
said shank having a bore formed therein, said bore extending longitudinally and coaxially throughout the entire length of said shank between said first and second ends, said bore having a first axial section with a non-circular cross-sectional shape adjacent said first end and a second axial section with a similarly-configured non-circular cross-sectional shape adjacent said second end, and a central section having a circular cross-section, intermediate said first and second axial sections.

27. A surgical interference screw according to claim 26 wherein said bore is configured to be engaged by a driver from said first and second ends alternatively.

28. In combination, a self-tapping surgical interference screw for interference securing of an end of a tendon or ligament within a bore in a bone, and a driver for simultaneously exerting axial force and torque on said screw, such that said screw is drawn into said bore and urges said end of the tendon or ligament into engagement with said bore,
said screw comprising an elongated body having a self-tapping thread formed on its outer surface and a bore formed extending through said body between first and second ends thereof, said screw being generally symmetric about a plane bisecting its axis of elongation, and at least both ends of said bore having substantially identical cross-sectional shapes for receiving torque from a driver having a corresponding cross-sectional shape inserted into said bore from either end thereof; and
said driver comprising:
a handle for receiving axial force and torque exerted by a user; and
an elongated shaft protruding from said handle, said shaft having (i) a distal tip terminating at a point of reduced cross-sectional area, (ii) a driving portion proximal to said tip, said driving portion being shaped to slide within said bore of said screw and transmit torque thereto, (iii) an extension portion spacing said driving portion from said handle, and (iv) a stop member separating said driving portion from said extension portion, said stop member limiting the distance said screw slides along said shaft, so that axial force can be transmitted from said driver to said screw,
wherein said stop member is spaced along said shaft from said tip by a distance corresponding to the length of said screw, such that said tip protrudes from a screw received on said driving portion and abutting said stop member.

29. The combination of claim 28, wherein said corresponding cross-sectional shapes of said bore in said screw and said driving portion of said shaft of said driver are hexagonal.

30. The combination of claim 28, wherein said bore in said screw includes first and second substantially similar end portions having said cross-sectional shape for receiving torque from said driver, and a cylindrical central section intermediate said end portions.

31. The combination of claim 28, wherein said tip defines a sharpened pick member.

32. The combination of claim 28, wherein said tip defines a twist drill.

33. The combination of claim 28, wherein said tip defines a trocar.

* * * * *